(12) United States Patent
Nix et al.

(10) Patent No.: US 11,351,358 B2
(45) Date of Patent: Jun. 7, 2022

(54) BLOOD PUMP

(71) Applicant: Abiomed Europe GMBH, Aachen (DE)

(72) Inventors: Christoph Nix, Aachen (DE); Katrin Lunze, Aachen (DE); Thorsten Siess, Aachen (DE); Walid Aboulhosn, Aachen (DE)

(73) Assignee: Abiomed Europe GMBH, Aachen (DE)

( * ) Notice: Subject to any disclaimer, the term of this patent is extended or adjusted under 35 U.S.C. 154(b) by 268 days.

(21) Appl. No.: 16/639,255

(22) PCT Filed: Aug. 17, 2018

(86) PCT No.: PCT/EP2018/072322
§ 371 (c)(1),
(2) Date: Feb. 14, 2020

(87) PCT Pub. No.: WO2019/034775
PCT Pub. Date: Feb. 21, 2019

(65) Prior Publication Data
US 2020/0246525 A1   Aug. 6, 2020

(30) Foreign Application Priority Data

Aug. 18, 2017 (EP) .................................... 17186897

(51) Int. Cl.
*A61M 60/13* (2021.01)
*A61M 60/546* (2021.01)
(Continued)

(52) U.S. Cl.
CPC .......... *A61M 60/50* (2021.01); *A61M 60/135* (2021.01); *A61M 60/148* (2021.01);
(Continued)

(58) Field of Classification Search
CPC .. A61M 60/50; A61M 60/148; A61M 60/414; A61M 60/135; A61M 60/562;
(Continued)

(56) References Cited

U.S. PATENT DOCUMENTS

| | | |
|---|---|---|
| 5,911,685 A | 6/1999 | Siess et al. |
| 2005/0071001 A1 | 3/2005 | Jarvik |

(Continued)

FOREIGN PATENT DOCUMENTS

| | | |
|---|---|---|
| WO | 9917819 A1 | 4/1999 |
| WO | 2005006975 A1 | 1/2005 |
| WO | 2010099411 A1 | 9/2010 |

OTHER PUBLICATIONS

International Search Report and Written Opinion for Application No. PCT/EP2018/072322 dated Nov. 8, 2018.

*Primary Examiner* — Erin M Piateski
(74) *Attorney, Agent, or Firm* — Botos Churchill IP Law LLP

(57) ABSTRACT

The invention concerns a control device for controlling a blood flow of an intravascular blood pump for percutaneous insertion into a patient's blood vessel, the blood pump comprising a pump unit with a drive unit for driving the pump unit and configured to convey blood from a blood flow inlet towards a blood flow outlet, wherein the control device is configured to operate the blood pump in a selectable zero-flow control mode, wherein a blood flow command signal is selected, and the control device comprises a first controller and a second controller, wherein the first controller is configured to control the blood flow by adjusting a speed command signal for the drive unit, and the second controller is configured to control a drive speed of the drive unit.

24 Claims, 4 Drawing Sheets

(51) Int. Cl.
*A61M 60/50* (2021.01)
*A61M 60/135* (2021.01)
*A61M 60/148* (2021.01)
*A61M 60/205* (2021.01)
*A61M 60/414* (2021.01)
*A61M 60/562* (2021.01)
*A61M 60/857* (2021.01)
*G16H 50/30* (2018.01)
*G16H 40/63* (2018.01)

(52) U.S. Cl.
CPC ........ *A61M 60/205* (2021.01); *A61M 60/414* (2021.01); *A61M 60/562* (2021.01); *A61M 60/857* (2021.01); *G16H 40/63* (2018.01); *G16H 50/30* (2018.01); *A61M 2205/3334* (2013.01); *A61M 2205/3365* (2013.01); *A61M 2205/50* (2013.01); *A61M 2230/04* (2013.01); *A61M 2230/30* (2013.01)

(58) Field of Classification Search
CPC .............. A61M 60/857; A61M 60/205; A61M 2205/3334; A61M 2205/3365; A61M 2205/50; A61M 2230/04; A61M 2230/30; G16H 50/30; G16H 40/63
USPC .......................................................... 600/17
See application file for complete search history.

(56) References Cited

U.S. PATENT DOCUMENTS

2005/0215843 A1* 9/2005 Medvedev ............ A61M 60/50
                                                    600/16
2017/0290967 A1* 10/2017 Botterbusch .......... A61F 2/2418
2019/0282741 A1* 9/2019 Franano ............... A61M 60/824

* cited by examiner

BLOOD PUMP

CROSS-REFERENCE TO RELATED APPLICATIONS

This application is a United States National Stage filing under 35 U.S.C. § 371 of International Application No. PCT/EP2018/072322, filed Aug. 17, 2018, which claims priority to European Patent Application No. 17186897.9, filed Aug. 18, 2017. The contents of each of each of the foregoing applications are hereby incorporated by reference in their entirety. International Application No. PCT/EP2018/072322 was published under PCT Article 21(2) in English.

FIELD OF THE INVENTION

The present invention concerns a blood pump, particularly an intravascular blood pump for percutaneous insertion into a patient's blood vessel. In particular, the invention relates to a specific control method of a percutaneous insertable blood pump, and a corresponding control device as well as a system comprising the control device and the blood pump. While the present invention is configured for and particularly useful for intravascular blood pumps, it is less relevant for larger blood pumps, such as VADs that are not placed inside a blood vessel or inside the heart, but outside the patient's heart, e.g. implanted in the thoracic cavity.

INTRODUCTION

Ventricular Assist Devices (VADs) are used to support the function of a patient's heart, either as a left ventricular assist device (LVAD) or right ventricular assist device (RVAD). While typical VADs are connected to the patient's heart by means of suitable conduits and are implanted into the patient's thoracic cavity outside the heart, an intravascular blood pump for percutaneous insertion typically comprises a catheter and a pump unit and is inserted through an access into a blood vessel and further into the patient's heart, e.g. through the aorta into the left ventricle. The pump unit may be located at the distal end of the catheter and comprises a blood flow inlet and a blood flow outlet and a cannula through which the blood flow is created e.g. by a rotor or impeller of the pump unit. For example, the cannula may extend through the aortic valve with the blood flow inlet disposed at a distal end of the cannula in the left ventricle and the blood flow outlet disposed at a proximal end of the cannula in the aorta. By creating the blood flow, the pressure difference between the outlet and the inlet is overcome.

An important aspect of intravascular blood pumps (hereinafter also simply referred to as "blood pumps"), amongst others, is explanting the intravascular blood pump from a patient and therefore affirming that the natural heart function has recovered. This may be done, for example, by adequately reducing the amount of assistance provided by the blood pump, so that the blood pump can be finally explanted once the heart is found sufficiently recovered. This aspect, i.e. determining the exact point in time for explantation, is not that important in larger VADs, which are typically implanted in a patient's thoracic cavity and designed for long-term applications.

Up to now, there is no physical signal known that sufficiently represents the status of heart recovery as long as an intravascular blood pump is implanted. While the blood pump is assisting the heart, it is not possible to know the unassisted heart function. And when the blood pump is switched off flow regurgitation through the cannula occurs so that it is impossible to know about the unassisted heart function. Regurgitation is particularly a problem of intravascular blood pumps because the blood pump, more specifically the pump's cannula, extends through a cardiac valve, e.g. the aortic valve, thereby creating an open path through the cardiac valve, which backflow into the heart when the blood pump is not driven. This issue typically does not occur in extravascular devices because they do not extend through a cardiac valve but by-pass the cardiac valve, such as VADs which are arranged outside the heart, e.g. in the thoracic cavity.

In the state-of-the-art the current pump speed setting is manually reduced by a physician gradually, e.g. by one level, based on professional experience. After reduction of the pump speed, the average aortic pressure is monitored. Some institutions perform echography based left ventricular volume assessments and continuous cardiac output measurements. If the mean aortic pressure remains stable it is assumed that the heart is able to take over work from the blood pump. However, if the mean aortic pressure drops, it is assumed that the heart still needs more assistance so that the pump speed needs to be increased again. Further, before blood pump explantation, a so-called on/off approach is applied. In doing so, the pump speed is significantly reduced, e.g. for some hours, in which the patient's physiological condition and the ventricular expansion in particular are observed, e.g. based on echocardiography (ECHO) measurements and/or cardiac ventriculography. ECHO may provide information on the heart such as size and shape, e.g. internal chamber size quantification, pumping capacity, and allow a calculation of the cardiac output, ejection fraction, and diastolic function. Cardiac ventriculography involves injecting contrast media into the heart's ventricle to measure the volume of blood pumped. Measurements obtained by cardiac ventriculography are ejection fraction, stroke volume, and cardiac output.

When the blood pump is switched off and if the heart still works insufficiently, the no longer assisted ventricle would significantly dilate so that not enough blood volume is ejected from the ventricle during the systolic phase, leading to an increase in left ventricular end-diastolic volumes and pressures. That is to say, due to the reduction of the pump speed the heart is loaded what may correspond to an acute overload of a still not recovered heart. This may result in a setback of the therapy of several days.

Thus, the actual monitoring process before explantation of a blood pump is more or less a trial-and-error procedure, in which, if the patient's condition remains stable, the pump speed is further reduced, and if it becomes worse, the pump speed needs to be increased again.

SUMMARY OF THE INVENTION

It is an object of the present invention to provide an improved control method and correspondingly improved control device for an intravascular blood pump as well as a system comprising the control device and an intravascular blood pump, wherein the blood pump can be operated such that a better assessment of the status of heart recovery can be ascertained.

The object is achieved by the features of the respective independent claims. Advantageous embodiments and further developments are defined in the respective dependent claims.

For sake of clarity, the following definitions will apply herein:

The term "characteristic parameter of the heart" is to be understood as a particular value derived from a physiological signal that is able to characterize a heart's condition with respect to, for example, loading, such as overloaded or unloaded, and/or a physiological condition, such as weak, strong, or recovered.

The "human circulatory system" is an organ system that permits blood to circulate. The essential components of the human circulatory system are the heart, blood and blood vessels. The circulatory system includes the pulmonary circulation, a "loop" through the lungs where blood is oxygenated; and the systemic circulation, a "loop" through the rest of the body to provide oxygenated blood.

The herein disclosed improvement concerns blood pumps that comprise settable blood flow levels. For example, in case of a rotational blood pump, "settable blood flow levels" may be discrete blood flow levels or continuously settable blood flow levels in a range defined by a minimum blood flow and a maximum blood flow.

The basic idea of the herein proposed control device and corresponding control method for controlling an intravascular blood pump is to provide a mode in which the current blood flow through the blood pump can be kept very low compared to its blood flow outlet capacity, preferably at zero. Preferably, the blood flow through the blood pump is kept between 0 and 1 L/min, more preferable between 0 and 0.5 L/min, between 0 and 0.2 L/min or even between 0 and 0.1 L/min. Most preferably, the blood flow through the blood pump is kept at about zero flow. In that case the blood pump is controlled such that it does neither produce a positive nor a negative blood flow. This operation mode is herein called "zero-flow control mode". For example, a zero-flow may be established and/or maintained by controlling a drive unit, e.g. a motor, of the blood pump, in particular the current drive speed of the drive unit, e.g. motor, and thereby the blood flow such that just the current pressure difference between the blood flow inlet and the blood flow outlet of the blood pump is compensated.

"Zero-flow" within this context has to be understood as zero flow or a very low blood flow. As the purpose of the zero-flow control mode is to achieve knowledge about a recovery status of the heart, it may also be adequate to perform a very low blood flow. A low blood flow, such as up to 0.1 L/min, up to 0.2 L/min or even up to 0.5 L/min, shall be regarded as "zero-flow" within this context. In any case "zero-flow" shall not be negative. In other words, the zero-flow shall not allow any back flow through the blood pump.

An intravascular blood pump for percutaneous insertion within this context comprises a catheter and a pump unit and is inserted into the patient's heart via a blood vessel, e.g. through the aorta into the left ventricle. The pump unit comprises a blood flow inlet and a blood flow outlet and a cannula through which the blood flow is created by a drive unit for driving the pump unit. For example, the pump unit may comprise a rotor or impeller that is driven by a drive unit, e.g. a motor, to convey blood from the blood flow inlet towards the blood flow outlet. For example, the cannula may extend through the aortic valve with the blood flow inlet disposed at a distal end of the cannula in the left ventricle and the blood flow outlet disposed at a proximal end of the cannula in the aorta. The intravascular blood pump may have a maximum outer diameter in the range of about 12 French (F) (about 4 mm) to about 21 French (F) (about 7 mm), e.g. 12 F (about 4 mm), 18 F (about 6 mm) or 21 F (about 7 mm), which typically is the maximum outer diameter of the pump unit. The catheter may have an outer diameter, which is less than that of the pump unit, e.g. 9 F (about 3 mm).

The natural heart function creates a pressure difference, for example between the aorta and the left ventricle. In order to create a positive blood flow, the blood pump has to overcome this pressure difference. Otherwise, i.e. if the pressure created by the blood pump is too low, the existing pressure difference between the aorta and the left ventricle will cause a backflow into the left ventricle.

By applying the zero-flow control mode, the blood pump does not supply assistance or very low assistance to the heart and advantageously avoids regurgitation, i.e. the blood pump does not allow a backflow of blood. For example, in case of left ventricle assistance, during diastole, the blood pump does not allow a black-flow of blood from the aorta back into the left ventricle.

By applying the zero-flow control mode, the drive unit of the blood pump, e.g. a rotor or impeller is still spinning. Thus, there is a reduced risk of thrombus formation due to the still moving parts.

By means of the zero-flow operation mode, the assistance provided by the blood pump to the heart is set to be basically zero. "Basically zero" means any blood flow still produced has to be at least negligible, but is in any case not negative, i.e. the blood pump does not allow back-flow through the blood pump.

In the zero-flow operation mode, the complete work in overcoming the pressure difference between the pressure in the assisted ventricle, e.g. the left ventricle, and the pressure in the adjacent blood vessel, e.g. the aorta, is provided solely by the heart. This way, the zero-flow operation mode allows monitoring one or more suitable characteristic parameters of the heart which may be used or interpreted as indicator for the status of the heart recovery.

Preferably, the blood flow of the blood pump is related to the drive speed of the drive unit, e.g. a motor, an electrical current supplied to the drive unit and/or the pressure difference between the outlet and the inlet of the blood pump. This relation can be stored in a memory, for example in a look-up table as will be described in more detail below. That is to say, command signal values can be stored in a memory of the control device or a memory in the blood pump accessible by the control device.

A first aspect provides a control device for controlling a blood flow $Q_{pump}(t)$ of an intravascular blood pump for percutaneous insertion into a patient's blood vessel. The blood pump comprises a pump unit and a drive unit for driving the pump unit that is configured to convey blood from a blood flow inlet towards a blood flow outlet. The control device is configured to operate the blood pump in a selectable zero-flow control mode, wherein a blood flow command signal $Q_{pump}^{set}(t)$ is selected. The control device comprises a first controller and a second controller, wherein the first controller is configured to control the blood flow $Q_{pump}(t)$ by adjusting a speed command signal $n_{pump}^{set}(t)$ for the drive unit, and the second controller is configured to control a drive speed $n_{pump}(t)$ of the drive unit. More specifically, the control device is particularly configured for controlling an intravascular blood pump, or more generally a low inertia device as will be described in more detail below.

Preferably, the intravascular blood pump comprises, between the blood flow inlet and the blood flow outlet, a cannula through which the blood flow is created by the pump unit. In operation, the cannula may extend for instance through the aortic valve, while the blood flow inlet is disposed in the left ventricle and the blood flow outlet is disposed in the aorta.

For example, the controlled blood flow can be constant. By compensating the current pressure difference between the blood flow inlet and the blood flow outlet the actual blood flow through the blood pump results in a zero-flow. That is to say, in the zero-flow control mode, a current pressure difference between the blood flow outlet and the blood flow inlet is counteracted by controlling the blood flow via control of the drive speed.

Preferably, the first controller is configured to determine the speed command signal $n_{pump}^{set}(t)$ based on a difference $\Delta Q$ between the blood flow command signal $Q_{pump}^{set}(t)$ and the blood flow $Q_{pump}(t)$. In other words, the first controller is configured to compare the actual blood flow $Q_{pump}(t)$ with the blood flow command signal $Q_{pump}^{set}(t)$ to determine the speed command signal $n_{pump}^{set}(t)$.

Preferably, the second controller is configured to control the drive speed $n_{pump}(t)$ by adjusting a drive current $I_{pump}(t)$ supplied to the drive unit. For example, the drive unit can comprise a motor, in particular an electric motor, and the adjusted drive current can be a motor current supplied to the motor. Thus, in case of a rotating drive unit the command speed signal $n_{pump}^{set}(t)$ and set drive speed $n_{pump}^{set}(t)$ of the drive unit can be a rotational speed. The motor may be located in the pump unit and directly or indirectly coupled to the impeller, e.g. by means of a mechanical connection or a magnetic coupling.

Preferably, the first controller and the second controller are part of a cascade control system, in which the first controller is an outer controller and the second controller is an inner controller. The outer controller may be embedded in outer control loop and may regulate the blood flow generated by the blood pump by comparing the blood flow command signal with the generated blood flow and by setting the set-point of an inner control loop, namely the speed command signal of the blood pump. The inner controller is part of the inner control loop and may control the speed of the blood pump by adjusting the motor current accordingly.

Preferably, the control device is configured to control the blood flow $Q_{pump}(t)$ for a predetermined zero-flow control period.

For example, the predetermined zero-flow control period may be set to last a fraction of one cardiac cycle of an assisted heart. That is, the zero-flow control mode is only briefly applied "within-a-beat". In this case, the predetermined zero-flow period is preferably small in comparison with the duration of the heart cycle. This way, information on the recovery status of the heart may be gathered without any overload of the heart since the duration without assistance to the heart is kept at a minimum.

For example, the predetermined zero-flow control period may be set to last at least one complete cardiac cycle or a predetermined number of complete consecutive heart cycles.

Preferably, the control device is configured to synchronize the zero-flow control period with an occurrence of at least one characteristic heart cycle event. For example, a beginning and/or end of the zero-flow control period is synchronized with the occurrence of the at least one characteristic heart cycle event. Particularly, the beginning and the end of the zero-flow control period may be synchronized with the occurrence of two characteristic heart cycle events. This way, the zero-flow control mode can be set to a time interval of the cardiac cycle in which a particular characteristic parameter of the heart may provide particular useful information which directly or indirectly indicates the status of heart recovery.

For example, the characteristic heart cycle events may be the opening of the aortic valve or the closing of the aortic valve. For example, the control device can be configured to detect the opening of the aortic valve by one of: presence of equilibrium of the left ventricular pressure and the aortic pressure, the occurrence of the R-wave in an electrocardiogram, ECG, signal led from the patient with the assisted heart.

Further characteristic heart cycle events may be the opening of the mitral valve, the closing of the mitral valve or the occurrence of an end diastolic left ventricular pressure.

Preferably, the control device is configured to monitor values of one or more characteristic heart parameters. That is, the control device can be configured to, in the zero-flow control mode, monitor one or more characteristic heart parameters, each time the zero-flow control mode is applied.

Preferably, the control device is configured to operate the intravascular blood pump in the zero-flow control mode periodically or randomly. The periodical or random application of the zero-flow control mode may be performed over a predetermined time span, e.g. from fractions of a heart cycle up to several days.

Preferably, the control device is configured to identify a trend of the one or more values of monitored characteristic heart parameters. The trend of the thereby monitored one or more characteristic heart parameters may be used as an indicator for the recovery status of the heart or the status of heart recovery as such, i.e. one may assist whether there is a progress in recovery at all. The trend may be indicated to a physician via a user interface of the control device so that the physician is enabled to decide on the heart recovery status.

For example, the at least one characteristic parameter of the heart can be the arterial blood pressure measured each time the zero-flow operation mode is established. By applying the zero-flow control mode the arterial blood pressure may drop. The pressure drop reaching a critical value or showing a critical decrease indicates that it is not possible to explant the blood pump as the heart hasn't recovered. In another example, the arterial blood pressure might stay stable or only shows a minor pressure drop during zero-flow control mode. In this case it can be assumed that the heart has sufficiently recovered, and the blood pump can be explanted.

Preferably, the at least one characteristic heart parameter is at least one of: the arterial pressure pulsatility $AOP|_{max}-AOP|_{min}$, the mean arterial pressure, the contractility of the heart $dLVP(t)/dt|_{max}$, the relaxation of the heart $dLVP(t)/dt|_{min}$, the heart rate HR.

The control device may be configured to measure the blood flow $Q_{pump}(t)$ by means of a sensor, to calculate or to estimate the blood flow $Q_{pump}(t)$. For example, the pressure difference between the blood flow outlet and the blood flow inlet may be determined by respective pressure sensors located at the inlet and the outlet of the blood pump, i.e. a pressure sensor capturing the after-load of the blood pump and a pressure sensor capturing the pre-load of the blood pump. The blood pump may comprise, alternatively or additionally, one sensor configured to measure just the pressure difference directly. Further in the alternative the pressure difference between the blood flow outlet and the blood flow inlet may be estimated, measured or calculated.

Rather than measuring the blood flow $Q_{pump}(t)$, the blood flow $Q_{pump}(t)$ may be determined using a look-up table, which may represent the relation between the blood flow, the drive speed, and at least one of a pressure difference between the blood flow outlet and the blood flow inlet and a drive current supplied to the drive unit. Such look up-table may include a set of characteristic curves which describe the respective relations, e.g. a set of curves, each for a certain pump speed. It will be appreciated that other suitable look-up tables may be used, and the values in the look-up tables may be given in various units.

Data for use in a look-up table, such as motor current and blood flow, can be recorded in a test bench assembly by running a blood pump in a fluid at a given motor speed and at a defined pump load (pressure difference between the inlet and the outlet) while recording the flow produced by the pump. The pump load can be increased over time, e.g. from zero load (no pressure difference between blood flow inlet and blood flow outlet, i.e. maximum flow) to maximum load (no pump function, i.e. no flow), while the motor current and blood flow are recorded. Such a look-up table may be created for several different motor speeds. Using such look-up table for determining the blood flow $Q_{pump}(t)$ may provide an advantageous way of determining the blood flow $Q_{pump}(t)$ during operation of the blood pumps, in particular compared to measuring or calculating the blood flow $Q_{pump}(t)$. With the look-up table, the blood flow $Q_{pump}(t)$ is determined based on easily available operation parameters of the blood pump only. Thus, no sensors for detecting parameters of the patient are necessary, such as pressure sensors for detecting a pressure difference inside the patient's vessel or flow sensors. Furthermore, reading a value for the blood flow $Q_{pump}(t)$ out of the look-up table does not require computationally intensive calculation.

However, monitoring the one or more suitable characteristic heart parameter just by applying the zero-flow control mode within-a-beat, the heart may not sufficiently adapt to the missing assistance of the blood pump. Thus, the monitored characteristic heart parameters may still not sufficiently indicate the true status of heart recovery, e.g. the actual pumping capacity of the heart. Thus, it is possible to repeat the zero-flow control mode within-a-beat in several consecutive heart cycles.

Thus, the predetermined zero-flow period can be set to last at least one complete cardiac cycle or a predetermined number of complete consecutive heart cycles. For example, the predetermined zero-flow period may be set to be a fraction of a heart cycle up to several hours. This way, the heart can fully adapt to the condition of zero assistance by the blood pump so that the actual status of heart recovery can be better ascertained.

It is also possible to combine zero-flow within-a-beat and over a complete heart cycle. For example, the zero-flow control mode may be applied at first for a relatively short time period, for example in a fraction of a heart cycle in 1 to 300 consecutive heart cycles. After acknowledgement of a natural heart function and a sufficient recovery status, the zero-flow control modes can be applied over a longer time period, such as over complete heart cycles for several minutes or hours up to days.

A second aspect provides a system comprising an intravascular blood pump for assistance of a heart and a control device according to the first aspect.

Preferably, the blood pump is catheter-based i.e. the blood pump preferably comprises a catheter and a pump unit, preferably with the pump unit located at a distal end of the catheter.

Preferably, the blood pump may be implemented as a rotational blood pump, i.e. a blood pump driven by a rotational motor.

The blood pump may be catheter-based to be implanted or placed directly percutaneously into a heart through corresponding blood vessels. For example, the blood pump may be a blood pump as published e.g. in U.S. Pat. No. 5,911,685, which is particularly arranged for a temporary placement or implantation into the left or right heart of a patient. As mentioned above, the present invention is particularly useful for intravascular blood pumps, and less relevant for larger VADs that are not placed inside a blood vessel or inside the heart, but outside the patient's heart, e.g. implanted in the thoracic cavity.

Preferably, the blood pump is a low inertia device. (a) The blood pump is a low inertia device by comprising one or more of the following characteristics; (b) Moving, in particular rotating, parts, for example a rotor or impeller, of the blood pump have low masses by being made of a low weight material, for example plastic; (c) The drive unit, such as an electric motor, is arranged near, preferably very near, most preferably adjacent, to a moving part, for example a rotor or impeller, of the pump unit driven by the drive unit; (d) If the blood pump is catheter-based, there is no rotational drive cable or drive wire. (e) A coupling or connection, for example a shaft, of the drive unit with a rotating part, for example the rotor or the impeller, of the pump unit driven by the drive unit is short; and (f) all moving, in particular rotating, parts of the blood pump have small diameters.

A low inertia device particularly includes an intravascular blood pump for percutaneous insertion into a patient's blood vessel. Because of their small diameter—in particular compared to relatively bulky VADs—all moving parts of intravascular blood pumps are low weight and are located near the rotational axis. This allows to control the pump speed in a very accurate manner since the rotation of the impeller is only marginally affected by the inertia of the impeller. That means, only slight delay occurs between the command signals and the actual response of the blood pump. In contrast to that, VADs designed for instance as centrifugal blood pumps may be bulky and may have a large diameter and, thus, a large rotor with higher mass and may not be referred to as "low inertia devices".

One characteristic for a low inertia device is, for instance, that reducing the pump speed of a low inertia device, in particular quickly reducing the pump speed, does not require a negative speed signal (which is typically necessary in large VADs) or other brake command, but reducing the motor current directly results in a reduced pump speed and the blood pump may be put into the zero-flow control mode simply by reducing the motor current. This is particularly relevant for the within-a-beat control as the cardiac cycle is very short and requires a short response time of the moving parts of the blood pump. Vice versa, it is likewise desirable to quickly accelerate the moving parts, i.e. to quickly increase the pump speed, in order to terminate the zero-flow control mode.

For instance, with a low inertia device in the sense of the present invention, it is possible to significantly increase or decrease the pump speed within a very short period of time, e.g. within about 50 ms to within about 100 ms, preferably 60 ms to 80 ms. In other words, the pump speed may quickly change or may make a "step change".

For instance, within said period of time the pump speed may be reduced from about 35,000 rpm to about 10,000 rpm, or in another blood pump from about 51,000 rpm to about 25,000 rpm, or vice versa accordingly increased. However, the duration of the pump speed change is also dependent on other factors like blood flow, pressure difference, intended amount of pump speed change (i.e. the difference between the pump speed before and after the intended speed change), or the point of time within the cardiac cycle (as the blood flow is accelerated during systole and slowed down during diastole).

A third aspect provides a method for controlling a blood flow $Q_{pump}(t)$ of an intravascular blood pump as discussed with the first aspect. That is, the blood pump comprises the pump unit with a drive unit and is configured to convey blood from a blood flow inlet towards a blood flow outlet. The method comprises the steps: (i) comparing a set blood flow value $Q_{pump}^{set}(t)$ with a blood flow value $Q_{pump}(t)$ resulting in a control error e(t) in a first closed-loop cycle; (ii) determining a set speed value $n_{pump}^{set}(t)$ for the drive means from the control error e(t); controlling a drive speed $n_{pump}(t)$ of the drive unit by comparing the set speed value $n_{pump}^{set}(t)$ with the drive speed $n_{pump}(t)$ in a second closed-loop cycle.

Preferably, the method further comprises the steps of providing a zero-flow mode in which the set blood flow value $Q_{pump}^{set}(t)$ is zero for a predetermined zero-flow control period, and preferably setting the predetermined zero-flow control period to last a fraction of one cardiac cycle of an assisted heart, or to last at least one complete cardiac cycle or a predetermined number of consecutive cardiac cycle fractions and/or complete cardiac cycles.

As described above in more detail with respect to the control device, the method may include the step of determining or estimating the blood flow $Q_{pump}(t)$ using an appropriate look-up table.

Preferably, the first closed-loop cycle is an outer control loop and the second closed-loop cycle is an inner control loop of a cascade control. The cascade control system including an outer control loop and an inner control loop has been described in more detail above with respect to the control device and are valid also for the method.

Preferably, the method further comprises: synchronizing the zero-flow control period with at least one particular characteristic heart cycle event.

Preferably, a beginning and/or an end of the zero-flow control period is synchronized with the occurrence of the at least one characteristic heart cycle event.

Preferably, the method further comprises: monitoring one or more values of characteristic heart parameters.

Preferably, the method further comprises: identifying a trend in the one or more monitored values of the characteristic heart parameters.

A fourth aspect provides the control device according to the first aspect which is configured to carry out the method according to the third aspect.

The above-discussed functions or functionalities of the control device and correspondingly of the control method can be implemented by a corresponding computing unit, in hardware or software or any combination thereof, of the control device. Such computing unit can be configured by means of corresponding computer programs with software code for causing the computing unit to perform the respectively required control steps. Such a programmable computing unit is basically well known in the art and to the person skilled in the art. Therefore, there is no need to describe such a programmable computing unit here in detail. Moreover, the computing unit may comprise particular dedicated hardware useful for particular functions, such as one or more signal processors for processing and/or analyzing e.g. the discussed measuring signals. Further, respective units for controlling the speed of a drive of the blood pump may be implemented by respective software modules as well.

The corresponding computer programs can be stored on a data carrier containing the computer program. Alternatively, the computer program may be transferred, e.g. via the Internet, in the form of a data stream comprising the computer program with-out the need of a data carrier.

BRIEF DESCRIPTION OF THE DRAWINGS

Hereinafter the invention will be explained by way of examples with reference to the accompanying drawings.

DETAILED DESCRIPTION

Figure 1:
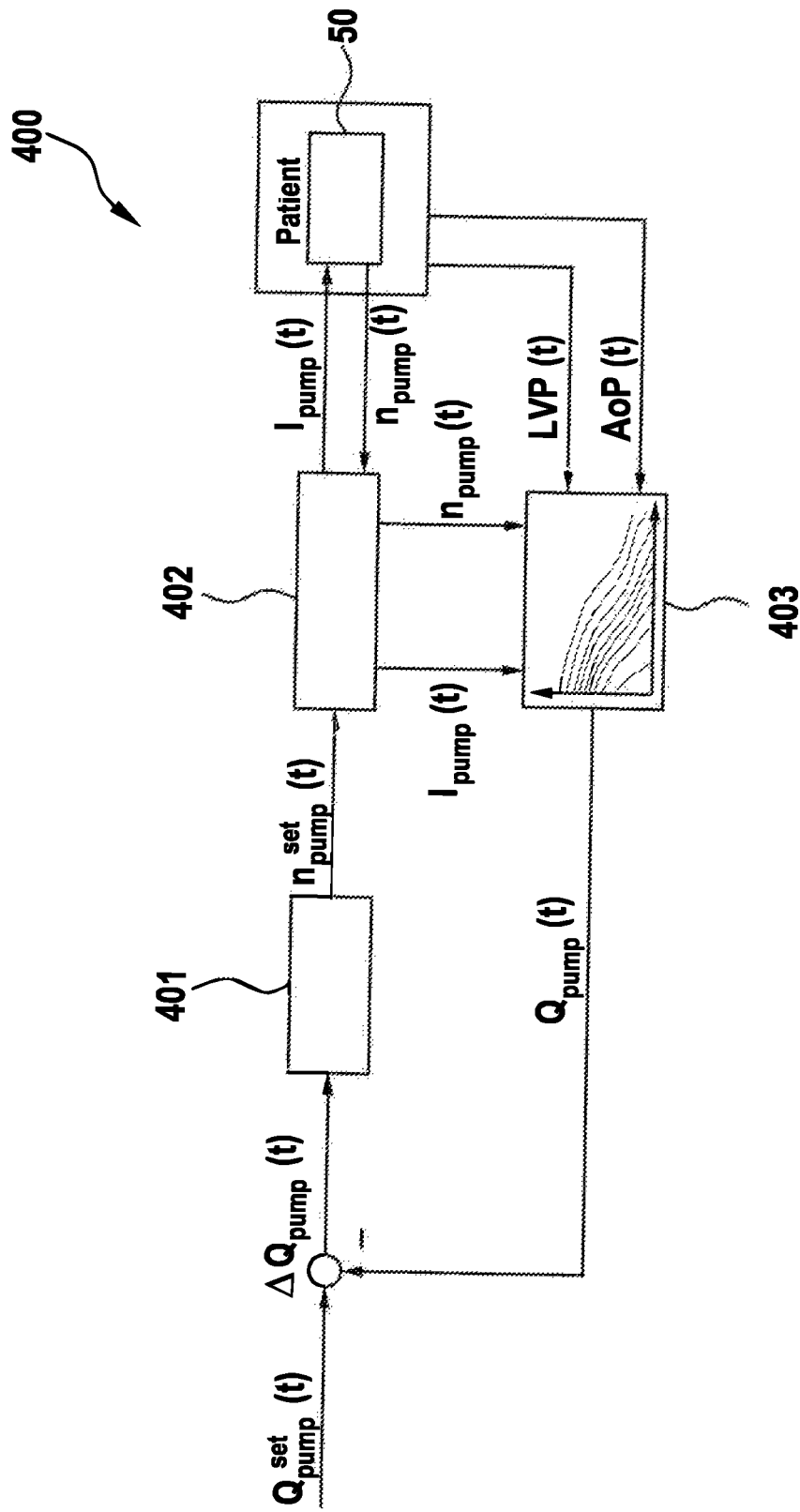
FIG. 1 shows a block diagram of a feedback control.

FIG. 1 shows a block diagram which is an example of the feedback control loop for blood flow control realized as a cascade control system. The control loop comprises an outer controller 401 and an inner controller 402. The outer controller 401 is embedded in outer control loop and regulates a generated blood flow $Q_{pump}(t)$ of e.g. the blood pump 50 shown in FIG. 3 by comparing a blood flow command signal $Q_{pump}^{set}(t)$ with the generated blood flow $Q_{pump}(t)$, and by setting the set-point of the inner control loop, namely the speed command signal $n_{pump}^{set}(t)$ of the blood pump 50. The inner controller 402 is part of the inner control loop and controls the speed $n_{pump}(t)$ of the blood pump 50 by adjusting a motor current $I_{pump}(t)$ accordingly.

In the feedback loop shown in FIG. 1, the generated blood flow $Q_{pump}(t)$ is exemplarily calculated by means of a look-up table which represents e.g. the relation of the electrical current $I_{pump}(t)$, the speed $n_{pump}(t)$ and the generated blood flow $Q_{pump}(t)$. Alternatively or additionally, another look-up table may be used to represent the relation of the pressure difference between the blood pump outlet 56 and the blood pump inlet 54 (cf. FIG. 3), the speed $n_{pump}(t)$ and the blood flow $Q_{pump}(t)$. Another alternative or additional option for data acquisition of the generated blood flow $Q_{pump}(t)$ is to use a flow sensor.

The flow control regulates the blood flow $Q_{pump}(t)$ through the blood pump 50 according to the blood flow command signal $Q_{pump}^{set}(t)$, which can be a constant value (also called set-value) or a changing signal over time. A constant blood flow set-value $Q_{pump}^{set}(t)$ may be in the range of [−5 . . . 10] L/min, preferably in the range of [0 . . . 5] L/min, and most preferably 0 L/min or a very low blood flow as zero-flow.

One of the aims of the here disclosed flow control is to monitor values of characteristic parameters of the heart with the implanted pump 50 for determining the recovery state of the heart while reducing the effect of the pump on the heart function. For this aim, the flow control may use a set blood flow $Q_{pump}^{set}(t)$ of 0 L/min or a very low blood flow as zero-flow.

It was found, that the inner control loop may have a small time constant relative to the outer control loop. This way, the inner control loop responds much faster than the outer control loop. In addition, the inner control loop may be performed at a higher sampling rate than the outer control loop.

For example, a sampling rate $fs_{IN}$ of the date in the inner control loop may be in the range of [250 . . . 10 k] Hz, preferably [1 . . . 3] kHz, and most preferably 2.5 kHz.

For example, a sampling rate $fs_{OUT}$ of the data in the outer control loop may be in the range of [25 . . . 1000] Hz, preferably [100 . . . 300] Hz, most preferably 250 Hz.

Figure 2:
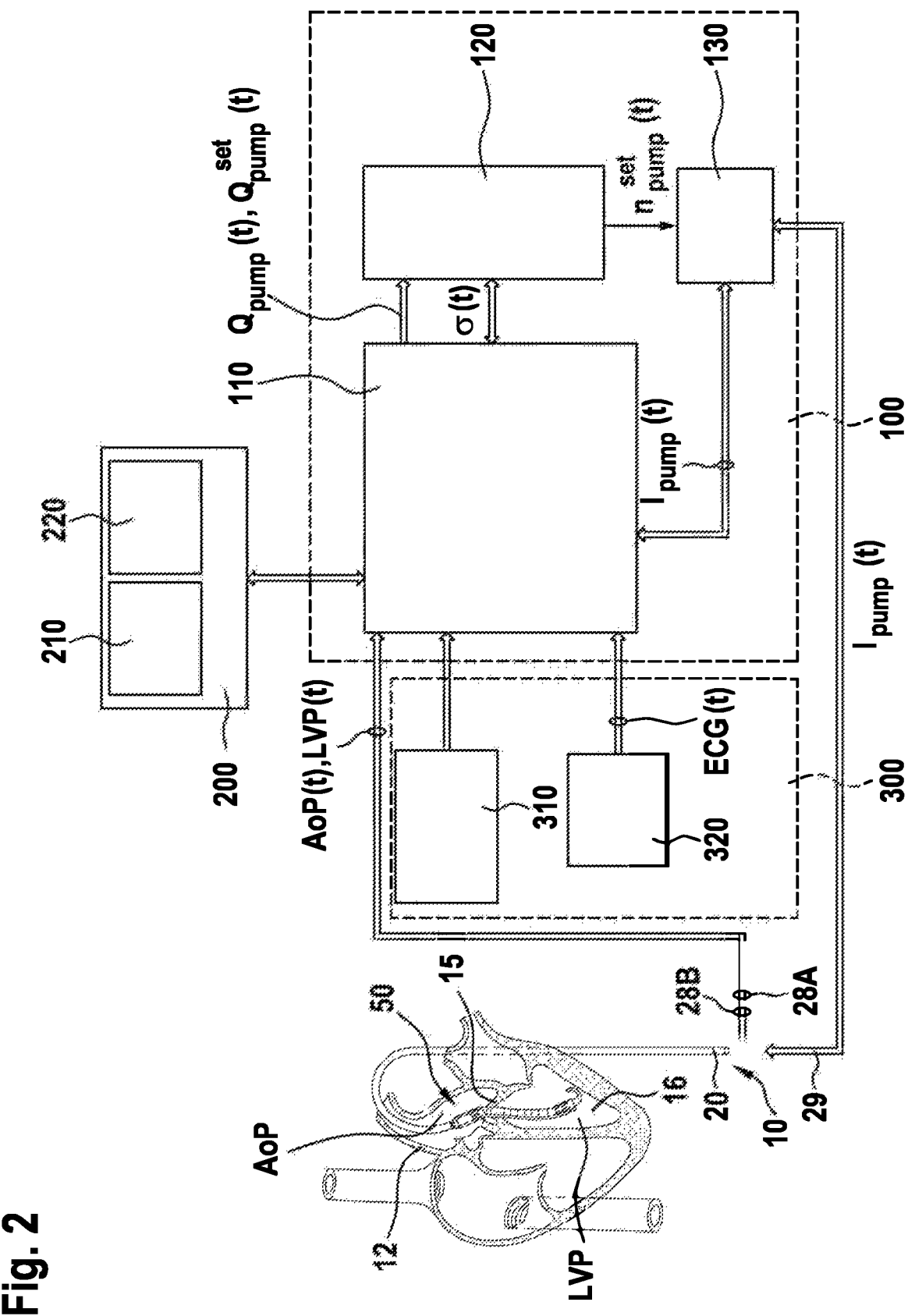
FIG. 2 shows an exemplary blood pump laid through the aorta and extending through the aortic valve into the left ventricle together with a block diagram of a control device for the pump speed of the blood pump.
Figure 3:
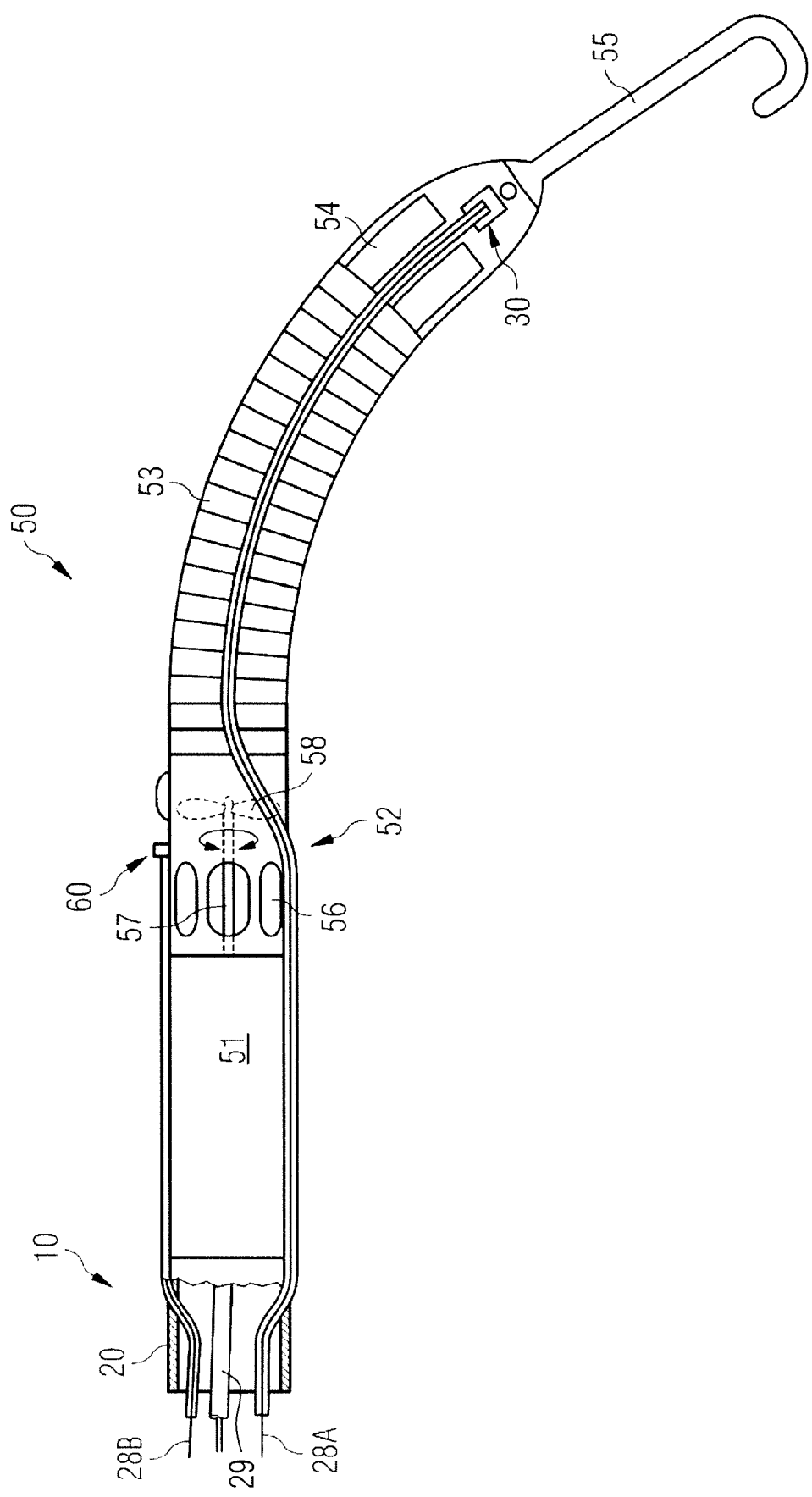
FIG. 3 shows the exemplary blood pump of FIG. 1 in more detail.

FIGS. 2 and 3 show an example for a blood pump. The blood pump is an intravascular blood pump configured for a percutaneous insertion into a heart. In the embodiment shown, the blood pump is a micro axial rotary blood pump, in the following for short called blood pump 50. Such a blood pump is, for example, known from U.S. Pat. No. 5,911,685 A.

The blood pump 50 is based on a catheter 20 by means of which the blood pump 50 can be temporarily introduced via a vessel into a ventricle of a patient's heart. The blood pump 50 comprises in addition to the catheter 20 a rotary drive unit 51 fastened to the catheter 20. The rotary drive unit 51 is coupled with a pump unit 52 located at an axial distance therefrom.

A flow cannula 53 is connected to the pump unit 52 at its one end, extends from the pump unit 52 and has blood flow inlet 54 located at its other end. The blood flow inlet 54 has attached thereto a soft and flexible tip 55.

The pump unit 52 comprises the pump housing with blood flow outlet 56. Further, the pump unit 52 comprises a drive shaft 57 protruding from the drive unit 51 into the pump housing of the pump unit 52. The drive shaft 57 drives an impeller 58 as a thrust element. During operation of the blood pump 50 blood is sucked through the blood flow inlet 54, conveyed through the cannula 53 and discharged through the blood flow outlet 56. The blood flow is generated by means of the rotating impeller 58 driven by the drive unit 51.

In the embodiment shown, through the catheter 20 pass three lines, namely two signal lines 28A, 28B and a power supply line 29 for suppling electrical power to the drive unit 51 of the blood pump 50. The signal lines 28A, 28B and the power-supply line 29 are attached at their proximal end to the control device 100 (FIG. 2). The signal lines 28A, 28B are associated with respective blood pressure sensors with corresponding sensor heads 30 and 60, respectively. The power supply line 29 comprises supply lines for supplying electrical power to the drive unit 51.

The drive unit 51 may be a synchronous motor. In an exemplary configuration the electrical motor may comprise several motor winding units for driving the impeller 58 that is coupled with the drive shaft 57. A rotor of the synchronous motor may comprise at least one field winding or, alternatively, a permanent magnet in case of a permanent magnet excited synchronous motor.

In a preferred embodiment, the blood pump 50 is a catheter-based micro axial rotational blood pump for percutaneous insertion through a patient's vessel into the patient's heart. Here, "micro" indicates that the size is small enough so that the blood pump can be percutaneously inserted into the heart, e.g. into one of the ventricles of the heart, via blood vessels leading to the heart. This also defines the blood pump 50 as an "intravascular" blood pump for percutaneous insertion. Here, "axial" indicates that the pump unit 52 and the drive unit 51 driving it are arranged in an axial configuration. Here, "rotational" means that the pump's functionality is based on a rotating operation of the trust element, i.e. the impeller 58, driven by the rotational electrical motor of the drive unit 51.

As discussed above, the blood pump 50 is based on the catheter 20 by which the insertion of the blood pump 50 through the vessels can be performed and through which the power supply line 29 can be passed for supplying electrical power to the drive unit 51 and control signals, e.g. from the drive unit 51 and the sensor heads 30, 60.

As mentioned above, the present invention is particularly configured for intravascular blood pumps, such as the blood pump 50 shown in FIG. 3, and less configured or even not suitable for VADs, which are implanted outside the patient's heart, e.g. centrifugal blood pumps connected to the patient's heart and placed in the thoracic cavity and operate in different ranges of pump speed. As explained herein, this is particularly because of inertia effects which significantly affect the function of large VADs but can be avoided in low inertia devices, such as intravascular blood pumps.

As shown in FIG. 2, each signal line 28A, 28B connects to one respective blood pressure sensor with the corresponding sensor head 30 and 60, respectively, which are located externally on the housing of the pump unit 52. The sensor head 60 of the first pressure sensor is connected with signal line 28B and is for measuring the blood pressure at the blood flow outlet 56. The sensor head 30 of the second blood pressure sensor is connected with signal line 28A and is for measuring the blood pressure at the blood flow inlet 54. Basically, signals captured by the pressure sensors, which carry the respective information on the pressure at the location of the sensor and which may be of any suitable physical origin, e.g. of optical, hydraulic or electrical, etc., origin, are transmitted via the respective signal lines 28A, 28B to corresponding inputs of a data processing unit 110 of the control device 100. In the example shown in FIG. 2, the blood pump 50 is positioned in the aorta and via the aortic valve in the left ventricle of the heart so that the pressure sensors are arranged for measuring the aortic pressure AoP(t) by sensor head 60 and the left ventricular pressure LVP(t) by sensor head 30.

The data processing unit 110 is configured for acquisition of external and internal signals, for signal processing, which includes for example calculation of a difference between pressure signals as a basis for estimating the generated blood flow $Q_{pump}(t)$ which may serve as control signal for the flow control approach, for signal analysis to detect the occurrence of characteristic events during the cardiac cycle based on the acquired and calculated signals, and for generating trigger signals σ(t) for triggering a speed command signal generator 120, just to name a few examples.

For the given example of a flow control approach, the speed command signal generator 120 represents the outer controller 401 in FIG. 1.

In the shown embodiment, the data processing unit 110 is connected via corresponding signal lines to additional measurement devices which are depicted in general by 300. Such additional measurement devices are, in the embodiment, a patient monitoring unit 310 and an electrocardiograph (ECG) 320; apparently, these two devices 310 and 320 are just two examples and not exhaustive, i.e. other measuring devices may be used for providing useful signals, as well. The depicted ECG 320 provides an ECG signal ECG(t) to the data processing unit 110.

The control device 100 further comprises a user interface 200. The user interface 200 for interaction with the user of the device. The user interface 200 comprises as output means a display 210 and as input means a communication interface 220. On the display 210, values of setting parameters, values of monitored parameters, such as measured pressure signals, and other information is displayed. Further, by the communication interface 220, the user of the control device 100 is enabled to take control of the control device 100, e.g. by changing the setup and settings of the whole system comprised of the blood pump and the control device 100.

For the given example of a flow control approach, a setting would be the choice of the desired pump flow $Q_{pump}^{set}(t)$ in FIG. 1.

The data processing unit 110 is particularly configured to derive or predict the time of occurrence of one or more predefined characteristic events during the cardiac cycle of the assisted heart. For example, the data processing unit 110 is configured to detect a predefined characteristic cardiac cycle event during the cardiac cycle by means of real-time analysis of monitored signals. Alternatively or additionally, a predefined characteristic cardiac cycle event, such as e.g. the R-wave, may be identified by the ECG signal from the ECG 320.

The occurrence of one or more determined predefined characteristic events are used for generation of a particular trigger signal σ(t) or a sequence of trigger signals σ(t). The resulting trigger signal σ(t) (or sequence thereof) is forwarded to the speed command signal generator 120 to correspondingly trigger speed command signal changes provided to a speed control unit 130.

In the context of the present invention, the speed command signal generator 120 is configured to operate the blood pump 50 in the zero-flow control mode.

The data processing unit 110 may be configured to predict the time of occurrence of the at least one predefined characteristic cardiac cycle event in an upcoming cardiac cycle based on the stored information about the characteristic cardiac cycle events occurring during the current and/or previous cardiac cycles, and analyze previous values of these speed command signals $n_{pump}^{set}(t)$, as well.

For example, a characteristic cardiac cycle event may be the beginning of contraction of the heart at the beginning of the systolic phase. The detected occurrence or the predicted occurrence of such characteristic cardiac cycle event can be used for synchronizing sequential applications of a particular control approach for the blood pump 50 within one or several cardiac cycles or within a particular time interval of the cardiac cycle.

Correspondingly, the speed command signal generator 120 is configured to adjust the speed command signal $n_{pump}^{set}(t)$ for the blood pump 50 to control the generated blood flow $Q_{pump}(t)$ according to a given blood flow command signal $Q_{pump}^{set}(t)$ which maybe set to be e.g. 0 L/min.

To control the generated blood flow $Q_{pump}(t)$, the speed command signal generator 120 is configured as an outer controller in the cascade control system to provide a suitable speed command signal $n_{pump}^{set}(t)$ to the speed control unit 130 either in a time-continuous way by continuously controlling the generated blood flow $Q_{pump}(t)$ (as a first setup) or in an event-based switching control manner (as a second setup).

In the first setup, the command signal generator 120 continuously provides the speed command signal $n_{pump}^{set}(t)$ to the speed control unit 130 as part of a cascaded blood-flow control system being fed with external and internal signals by the data processing unit 110.

In the second setup, the speed command signal generator 120 operates as in the first setup with the additional feature to switch the continuous blood flow control on and off.

In the zero-flow control mode, the speed command signal $n_{pump}^{set}(t)$ is continuously adjusted by the flow controller in the outer control loop. The on/off switching is triggered by at least one trigger signal σ(t) provided by the data processing unit 110.

The second setup is suitable, if the zero-flow control is just applied for a short time interval, in particular short compared with the duration of one cardiac cycle; in other words, the generated blood flow is controlled with a blood flow command signal $Q_{pump}^{set}(t)$ 0 L/min just for a brief time interval within the cardiac cycle (within-a-beat blood flow control).

The speed control unit 130 controls the speed $n_{pump}(t)$ of the blood pump 50, in accordance with the speed command signal $n_{pump}^{set}(r)$, by supplying an electrical current $I_{pump}(t)$ to the drive unit 51 of the blood pump 50 via the power-supply line 29.

The current level of the supplied motor current $I_{pump}(t)$ corresponds to the electrical current currently required by e.g. an electrical motor of the drive unit 51 to establish a target speed level as defined by the speed command signal $n_{pump}^{set}(t)$. A measuring signal such as the supplied motor current $I_{pump}(t)$ can be used as a representative signal of an internal signal of the control device 100 and may be provided to the data processing unit 110 for further processing. Via the power-supply line 29, the blood pump 50 may also communicate with the control unit 100.

Basically, amongst others, the control device 100 is configured to operate the blood pump 50 in the selectable zero-flow control mode, in which the blood flow $Q_{pump}(t)$ of the blood pump 50 is controlled to counteract the changing pressure difference between the blood outlet 56 and the blood inlet 54 due to heart beat which can be regarded as disturbance. The blood flow $Q_{pump}(t)$ is controlled by adjusting the speed command signal $n_{pump}^{set}(t)$. As proposed herein, the control device 100 is configured to control the blood flow $Q_{pump}(t)$ of the blood pump 50 such that the blood pump 50 generates zero blood flow for a predetermined zero-flow control period.

In the first setup with continuous flow control, the predetermined zero-flow control period is set to last at least one complete cardiac cycle or a predetermined number of complete consecutive heart cycles. Further in the first setup, the control device 100 is configured to monitor the values of one or more characteristic heart parameters with the implanted blood pump 50. Again, the monitored values of one or more characteristic heart parameters can be used as an indicator for the status of heart recovery.

In the second setup with an event-based zero-flow control, the predetermined zero-flow control period is set to be a fraction of the duration of one cardiac cycle of the heart with the implanted blood pump 50. In this setup, the control device 100 is configured to synchronize the beginning and the end of the zero-flow control period with the occurrence of a particular characteristic heart cycle event.

Notably, the control device 100 may control the blood flow $Q_{pump}(t)$ through the blood pump 50 periodically or randomly.

In a particular implementation, a characteristic heart cycle event is the opening of the aortic valve or the closing of the aortic valve or the opening of the mitral valve or the closing of the mitral valve, or particular pressure values as the end-diastolic left ventricular pressure.

Further in the second set-up, as in the first setup, the control device 100 is configured to monitor the values of one or more characteristic heart parameters of the heart with the implanted blood pump 50 during the zero-flow control period. The monitored values of one or more characteristic heart parameters can be used as an indicator for the status of heart recovery, as well.

The control device 100 is further configured to identify a trend in the values of one or more monitored characteristic parameters. As mentioned herein above, the trend can be interpreted as an indicator for the status of heart recovery, too.

In any case, for implementing the zero-flow control mode, the control device 100 is configured to control the blood flow $Q_{pump}(t)$ by adjusting the speed command signal $n_{pump}^{set}(t)$ of the blood pump 50 whereby the drive speed $n_{pump}(t)$ is affected by the changing blood pressure difference between the blood flow outlet 56 of the blood pump 50 and the blood flow inlet 54 of the blood pump 50 during the cardiac cycle.

Particularly, the control device 100 is configured to determine the blood flow $Q_{pump}(t)$ of the blood pump 50 based on predetermined signals as e.g. the drive speed $n_{pump}(t)$, the electrical current $I_{pump}(t)$ and/or the pressure difference between the blood flow outlet 56 and the blood flow inlet 54 of the blood pump 50.

Figure 4:
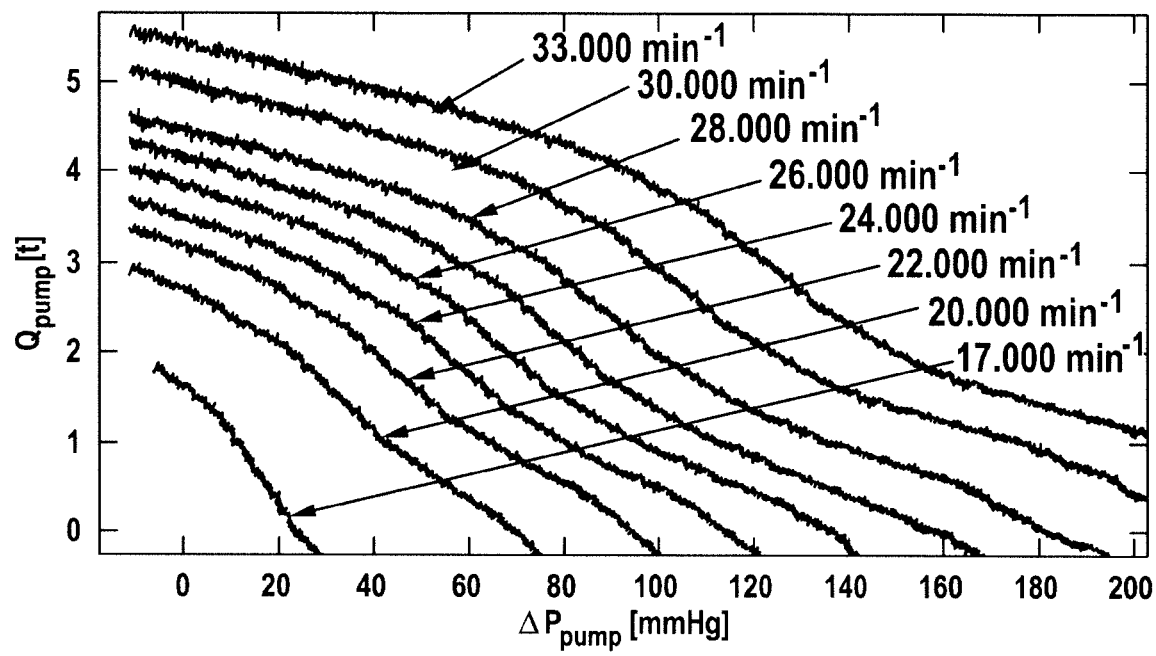
FIG. 4 is an exemplary diagram showing a set of characteristic curves representing the relationship between the actual pressure difference between the in-take and the outlet of the blood pump, the actual pump speed of the blood pump, and the blood flow produced through the blood pump.

FIG. 4 is an exemplary diagram showing a set of characteristic curves representing the relationship between the pressure difference $\Delta P_{pump}(t)$ between the blood flow outlet 56 and the blood flow inlet 54 of the blood pump 50, the drive speed $n_{pump}(t)$ of the blood pump 50, and the blood flow $Q_{pump}(t)$ generated by the blood pump 50, e.g. through the flow cannula 53 in FIG. 3.

In order to perform the zero-flow control, the data processing unit 110 is configured to continuously determine the blood flow $Q_{pump}(t)$ generated by the blood pump 50, based on the known the speed $n_{pump}(t)$, the known electrical current $I_{pump}(t)$ supplied to the pump unit 51 and/or the monitored pressure difference $\Delta P_{pump}(t)$ between the blood flow outlet 56 and the blood flow inlet 54 of the blood pump 50. A set blood flow value $Q_{pump}^{set}(t)$ could be zero or at least a positive value close to zero.

For example, based on FIG. 4, in the case, the monitored pressure difference $\Delta P_{pump}(t)$ between the blood flow outlet 56 and the blood flow inlet 54 of the blood pump 50 is 60 mmHg, the drive speed $n_{pump}(t)$ has to be at about 20.000 1/min (rpm) to generate a blood flow $Q_{pump}(t)$ of about 0 L/min.

It will be appreciated that the values, relationships and shapes of the curves shown in the characteristic diagram of FIG. 4 are only exemplary and may vary depending on the used blood pump, patient or other factors. In particular, each and every blood pump, even blood pumps of the same type, may have individual characteristic diagrams, i.e. the look-up table may be pump specific. Furthermore, once implanted in a patient, the characteristic diagram might have to be adapted by means of a patient specific correction factor, including various factors like viscosity of the blood, location of the blood pump etc. Using a correction factor may increase the accuracy of the flow estimation obtained from the look-up table.

As discussed before, the current pressure difference $\Delta P_{pump}(t)$ can be determined by means of pressure sensors (e.g. sensors 30, 60, FIG. 3) of the blood pump 50. Thus, speed control unit 130 can be continuously provided with values out of storage unit, e.g. a look-up table in which the characteristic curves of FIG. 4 (here representing the relationship between the above-discussed values $\Delta P_{pump}(t)$, $Q_{pump}(t)$, and $n_{pump}(t)$) are stored. The storage unit may be a read only memory of the data processing unit 110 or, alternatively, a storage chip in the blood pump 50 or in the control console 130 thereof.

The at least one characteristic heart parameter value is at least one of: the arterial blood pressure measured each time the zero-flow operation mode is established.

Preferably, the blood pump 50 is a low inertia device. This particularly achieved in that moving, in particular rotating, parts, for example a rotor or impeller, of the blood pump 50 comprise low masses, by being made of a low weight material, for example plastic. Additionally, the drive unit, such as an electric motor, is arranged near, preferably very near, most preferably adjacent, to a part, such as the trust element, for example a rotor or impeller 58, driven by the drive unit. Additionally, even though the blood pump 50 is catheter-based, there is no rotational drive cable or drive wire. Additionally, a coupling or connection, for example the shaft 57, of the drive unit 51 with the trust element, for example a rotor or impeller 58, driven by the drive unit 51 is kept short. Additionally, all moving, in particular rotating, parts of the blood pump 50 have small diameters.

Summarizing, in the herein proposed zero-flow control approach, the control device 100 controls the generated blood flow $Q_{pump}(t)$ through the blood pump 50 in a cascade control consisting of an outer and an inner control loop. That means the generated blood flow $Q_{pump}(t)$ through the blood pump 50 is controlled by adjusting the speed command signal $n_{pump}^{set}(t)$ for the drive unit 51 of the blood pump 50 in the outer control loop, and the drive speed $n_{pump}(t)$ by adjusting the electrical current $I_{pump}(t)$ is controlled in the inner control loop. The zero-flow control approach is either applied continuously or partly continuously, i.e. the zero-flow control period lasts either one or several complete cardiac cycles or just a fraction of a cardiac cycle. In the case, that the predetermined zero-flow control period lasts just a portion of the duration of the cardiac cycle, the zero-flow control period may be synchronized with the heartbeat by means of at least one characteristic event of the cardiac cycle.

We claim:

1. A control device for controlling a blood flow of an intravascular blood pump for percutaneous insertion into a patient's blood vessel, the blood pump comprising a pump unit and a drive unit for driving the pump unit that is configured to convey blood from a blood flow inlet towards a blood flow outlet wherein
   the control device is configured to operate the blood pump in a selectable zero-flow control mode for a predetermined zero-flow control period, wherein a blood flow command signal is selected, and the control device comprises a first controller and a second controller, wherein
   the first controller is configured to control the blood flow by adjusting a speed command signal for the drive unit, and the second controller is configured to control a drive speed of the drive unit.

2. The control device of claim 1, wherein the first controller is further configured to determine the speed command signal based on a difference between the blood flow command signal and the blood flow.

3. The control device claim 1, wherein the second controller is configured to control the drive speed by adjusting a drive current supplied to the drive unit.

4. The control device of claim 1, wherein the first controller and the second controller are part of a cascade control system, in which the first controller is an outer controller and the second controller is an inner controller.

5. The control device of claim 1, wherein
   the predetermined zero-flow control period is set to last a fraction of one cardiac cycle of an assisted heart; or the predetermined zero-flow control period is set to last at least one complete cardiac cycle or a predetermined number of complete consecutive heart cycles.

6. The control device of claim 5, wherein the control device (100) is configured to synchronize the predetermined zero-flow control period with an occurrence of at least one characteristic heart cycle event.

7. The control device of claim 6, wherein at least one of a beginning or an end of the predetermined zero-flow control period is synchronized with the occurrence of the at least one characteristic heart cycle event.

8. The control device of claim 7, wherein the at least one characteristic heart cycle event is opening of an aortic valve or closing of the aortic valve.

9. The control device of claim 1, wherein the control device is configured to monitor values of one or more characteristic heart parameters.

10. The control device of claim 9, wherein the control device is configured to operate the blood pump in the selectable zero-flow control mode periodically or randomly.

11. The control device of claim 10, wherein the control device is configured to identify a trend of the one or more values of monitored characteristic heart parameters.

12. The control device of claim 11, wherein the monitored characteristic heart parameter is at least one of: arterial pressure pulsatility, mean arterial pressure, contractility of a heart, relaxation of the heart, or heart rate HR.

13. The control device of claim 1, wherein the control device is configured to measure the blood flow by means of a sensor or to calculate or estimate the blood flow.

14. The control device of claim 1, wherein the control device is configured to determine the blood flow using a look-up table which represents a relation between the blood flow, the drive speed, and at least one of a pressure difference between the blood flow outlet and the blood flow inlet or a drive current supplied to the drive unit.

15. A system comprising an intravascular blood pump for percutaneous insertion into a patient's blood vessel and a control device for controlling a blood flow of the intravascular blood pump, the blood pump comprising a pump unit and a drive unit for driving the pump unit that is configure to convey blood from a blood flow inlet toward a blood flow outlet,
wherein the control device is configured to operate the blood pump in a selectable zero-flow control mode for a predetermined zero flow control period wherein a blood flow command signal is selected, and the control device comprises a first controller and a second controller,
wherein the first controller is configured to control the blood flow by adjusting a speed command signal for the drive unit, and the second controller is configured to control a drive speed of the drive unit.

16. The system of claim 15, wherein the blood pump comprises one or more moving parts and is a low inertia device having one or more of the following characteristics: the one or more moving parts of the blood pump being made of a low weight material; the drive unit being arranged near to at least one moving part of the one or more moving parts of the blood pump without a rotational drive cable; the drive unit being coupled by a short connection to at least one moving part of the one or more moving parts; and the one or more moving parts of the blood pump having small diameters.

17. A method for controlling a blood flow of an intravascular blood pump for percutaneous insertion into a patient's blood vessel, the blood pump comprising a pump unit with a drive unit and being configured to convey blood from a blood flow inlet towards a blood flow outlet, wherein the method comprises the steps:
comparing a set blood flow value with a blood flow value resulting in a control error in a first closed-loop cycle,
determining a set speed value for a drive means from the control error,
controlling a drive speed of the drive unit by comparing the set speed value with the drive speed in a second closed-loop cycle
providing a zero-flow mode in which the set blood flow value is zero for a predetermined zero-flow control period.

18. The method of claim 17, wherein the first closed-loop cycle is an outer control loop and the second closed-loop cycle is an inner control loop of a cascade control.

19. The method of claim 17, further comprising:
synchronizing the predetermined zero-flow control period with at least one particular characteristic heart cycle event.

20. The method of claim 19, wherein at least one of a beginning or an end of the predetermined zero-flow control period is synchronized with an occurrence of the at least one particular characteristic heart cycle event.

21. The method of claim 17, further comprising:
monitoring one or more values of characteristic heart parameters.

22. The method of claim 21, further comprising:
identifying a trend in the one or more monitored values of the characteristic heart parameters.

23. The system of claim 16, wherein the one or more moving parts of the blood pump comprises a rotor or an impeller.

24. The method of claim 17, further comprising:
setting the predetermined zero-flow control period to last a fraction of one cardiac cycle of an assisted heart, or to last a least one complete cardiac cycle or a predetermined number of at least one of consecutive cardiac cycle fractions or complete cardiac cycles.

* * * * *

UNITED STATES PATENT AND TRADEMARK OFFICE
CERTIFICATE OF CORRECTION

PATENT NO. : 11,351,358 B2
APPLICATION NO. : 16/639255
DATED : June 7, 2022
INVENTOR(S) : Christoph Nix et al.

It is certified that error appears in the above-identified patent and that said Letters Patent is hereby corrected as shown below:

In the Specification

Column 14, Line 10:
Now reads: "0 L/min"; should read --of 0 L/min--

Column 14, Line 15:
Now reads: "$n_{pump}^{set}(r)$,"; should read --$n_{pump}^{set}(t)$,--

Column 15, Line 33:
Now reads: "51"; should read --52--

In the Claims

Column 16, Claim 3, Line 58:
Now reads: "device", should read --device of--

Column 17, Claim 6, Line 5:
Now reads: "device (100)", should read --device--

Column 18, Claim 17, Line 23:
Now reads: "cycle", should read --cycle, and--

Signed and Sealed this
Third Day of January, 2023

Katherine Kelly Vidal
*Director of the United States Patent and Trademark Office*